United States Patent [19]

Mills et al.

[11] Patent Number: 4,812,239

[45] Date of Patent: Mar. 14, 1989

[54] DRY CHEMICAL MIX SYSTEM FOR HEMODIALYSIS

[75] Inventors: Gary N. Mills, Gladstone; Charles B. Willock, Milwaukie, both of Oreg.

[73] Assignee: CD Medical Inc., Miami Lakes, Fla.

[21] Appl. No.: 51,054

[22] Filed: May 15, 1987

[51] Int. Cl.[4] ............................................. B01D 13/00
[52] U.S. Cl. .................................... 210/647; 210/96.2
[58] Field of Search ................. 366/279, 343, 328, 21, 366/28; 210/169, 647, 34.3, 96.2, 34.1; 422/265, 279, 269

[56] References Cited

U.S. PATENT DOCUMENTS

| | | | |
|---|---|---|---|
| 2,800,152 | 7/1957 | Sloier | 141/104 |
| 2,802,599 | 8/1957 | Callahan et al. | 222/1 |
| 3,084,047 | 4/1963 | Holstein et al. | 99/65 |
| 3,207,365 | 9/1965 | Burford et al. | 222/1 |
| 3,352,779 | 11/1967 | Austin et al. | 210/96.2 X |
| 3,425,398 | 10/1966 | Buffy et al. | 119/51.11 |
| 3,490,591 | 1/1970 | Jones et al. | 210/85 |
| 3,598,727 | 4/1969 | Willock | 210/22 |
| 3,744,636 | 7/1973 | Commarmot | 210/180 |
| 3,802,562 | 4/1974 | Kozlov et al. | 210/96 |
| 3,847,809 | 11/1974 | Kopf | 210/96 X |
| 4,082,667 | 4/1978 | Seiler, Jr. | 137/92 X |
| 4,103,357 | 7/1978 | Noguchi et al. | 366/152 |
| 4,107,039 | 8/1978 | Lindsay, Jr. et al. | 210/90 |
| 4,136,708 | 1/1979 | Cosentino et al. | 137/99 |
| 4,172,033 | 10/1979 | Willock | 210/91 |
| 4,202,760 | 5/1980 | Storey et al. | 210/96.2 X |
| 4,293,409 | 10/1981 | Riede et al. | 210/96.2 |
| 4,399,036 | 8/1983 | Babb et al. | 210/638 |
| 4,493,249 | 1/1985 | Stover | 99/275 |
| 4,508,622 | 4/1985 | Polaschegg et al. | 210/96.2 |
| 4,536,092 | 8/1985 | Kedem | 366/279 X |
| 4,734,198 | 3/1988 | Harm et al. | 210/647 |

OTHER PUBLICATIONS

Renapak brochure, "Renapak Concentrate Manufacturing System," by Renal Systems, Inc.

Primary Examiner—Frank Spear

[57] ABSTRACT

An apparatus for preparing dialysate solution directly from a dry chemical mix for continuous supply to a dialysis machine is disclosed. The preferred embodiment includes a drum for containing the dry chemical mix, a conveyor belt, a mixing vessel and monitoring equipment. The drum includes internal baffles that cause the dry chemical to be deposited onto the end of the conveyor belt as the drum rotates. The conveyor belt passes the chemical through a profile-determining gate and into the top of a funnel-shaped mixing vessel. The rate at which the conveyor belt delivers the chemical to the mixing vessel is governed by an electronic circuit that measures the conductivity of the dissolved solution and adjusts the belt speed as necessary to maintain the conductivity at a set value. The dissolved solution flows out the side of the mixing vessel and into a flow controller which regulates the rate at which dialysate can be withdrawn.

5 Claims, 4 Drawing Sheets

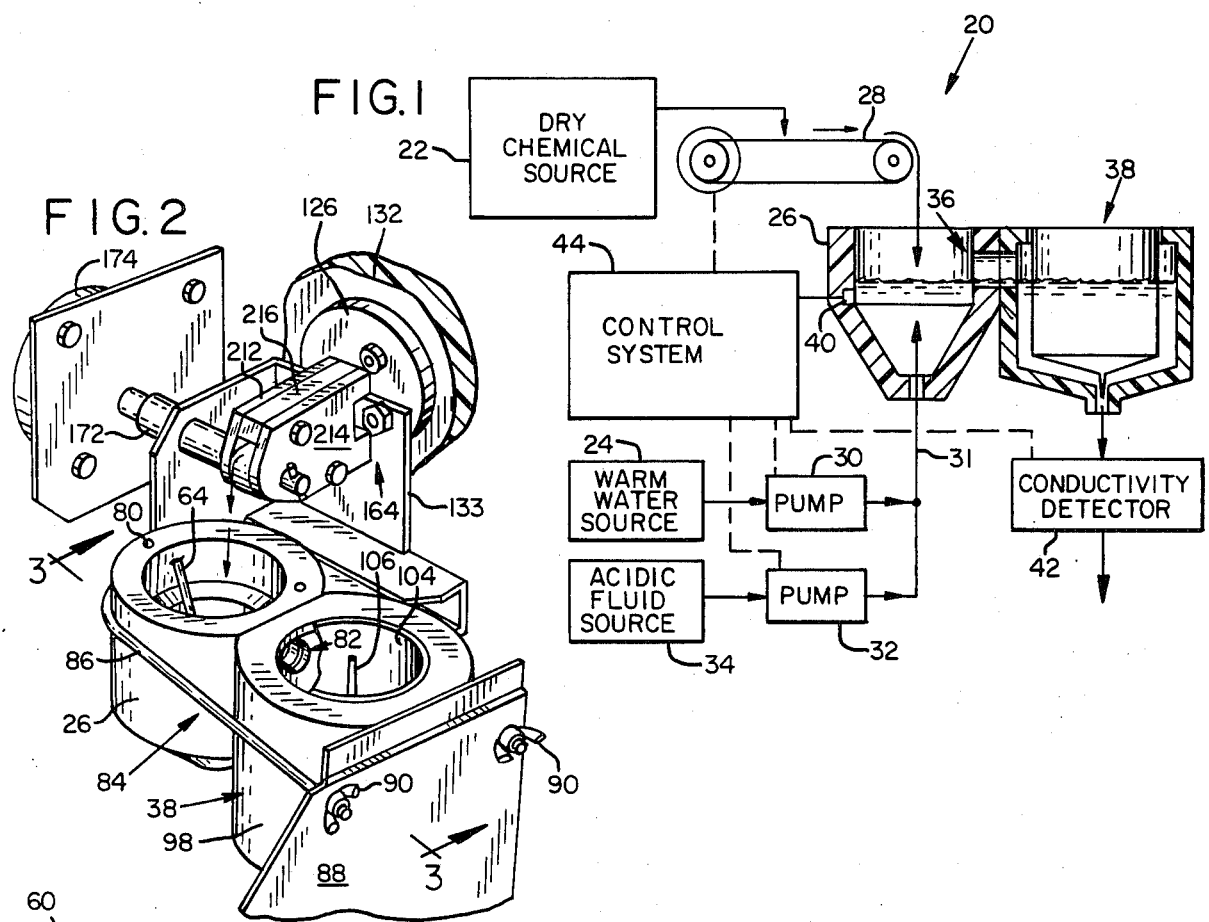
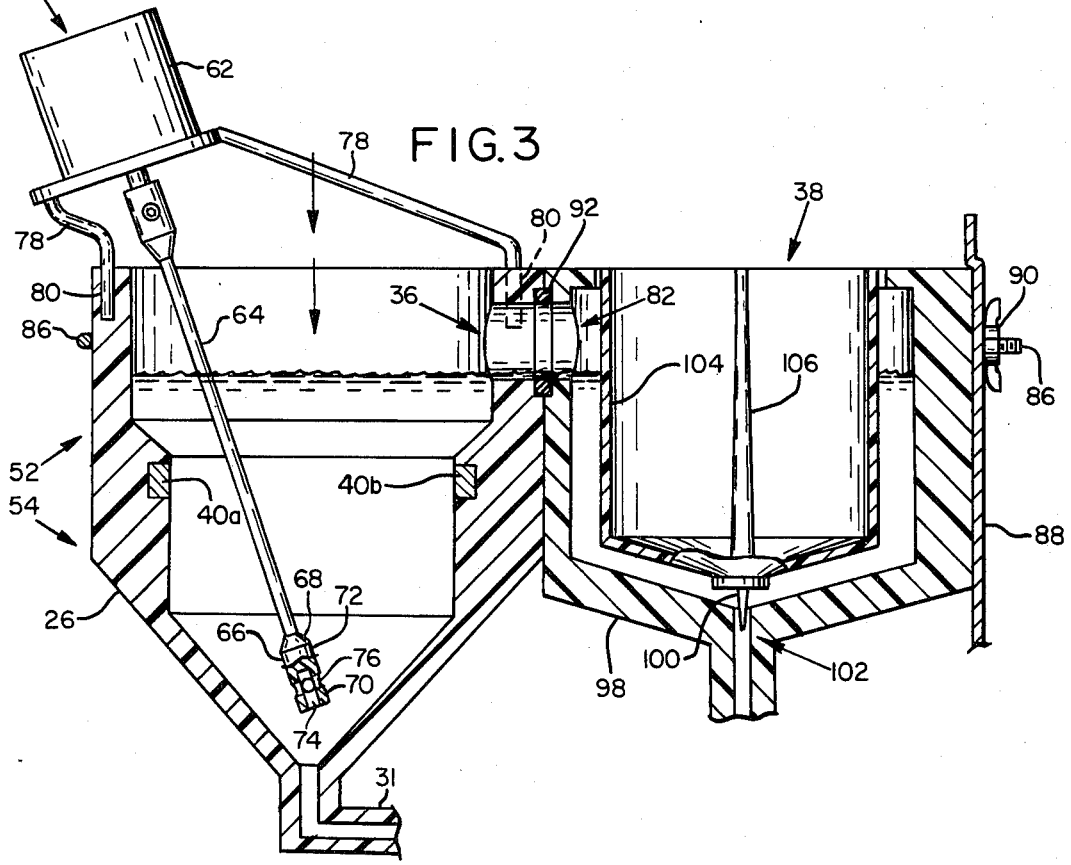

DRY CHEMICAL MIX SYSTEM FOR HEMODIALYSIS

TECHNICAL FIELD

The present invention relates to the continuous dissolution of a dry chemical mix into a liquid so as to form dialysate solution useful in hemodialysis therapy.

BACKGROUND AND SUMMARY OF THE INVENTION

Dialysate solution used in hemodialysis therapy is generally formed by mixing together controlled proportions of liquid dialysate concentrate and water using a "proportioning system." A first type of proportioning system, exemplified by U.S. Pat. Nos. 3,598,727 and 4,172,033 to Willock, 4,107,039 to Lindsay, Jr. et al. and 4,136,708 to Cosentino et al., operates by volumetrically metering liquid concentrate and water to a mixing point using positive displacement piston pumps. The precise ratio of liquid concentrate to water is generally determined by the relative volumes of the pump chambers and in some systems can be varied somewhat by varying the relative travels of the pump pistons.

A second type of proportioning system, exemplified by U.S. Pat. Nos. 4,202,760 to Storey et al., 4,293,409 to Riede et al., 4,508,622 to Polaschegg et al., 3,847,809 to Kopf and 4,082,667 to Seiler, Jr., produces dialysate by introducing dialysate concentrate at a controlled rate into a flow of water. The conductivity of the resulting dialysate is detected downstream from the mix point and is used to regulate the rate at which the liquid concentrate is introduced into the flow of water.

Dialysate proportioning systems are generally included as integral parts of hemodialysis therapy machines, serving to mix the dialysate solution on-line as part of the machine's operation. Preparation of the liquid concentrate used in such systems, however, is an off-line, batch process performed either by the operator of the dialysis machine or by a third party concentrate vendor. In either case, the process is the same. A dry chemical mix of selected salts and other components is dissolved in a large tank of water. Dissolution of the dry chemical mix is effected by a mechanical stirring element or by a recirculation pump that withdraws water from the tank and forcibly reintroduces it, thereby causing turbulence that promotes dissolution. Undissolved chemical that settles to the bottom of the tank, however, tends to collect adjacent the sidewalls where it is not readily dissolved by recirculation or stirrer techniques. Exemplary of the apparatuses used to prepare concentrate is the Renapak Concentrate Manufacturing System marketed by Renal Systems, Inc.

The current practice of preparing dialysate from liquid concentrate suffers from a number of drawbacks. First is the need for complex hydraulic equipment in those proportioning systems that rely on volumetric metering of the components to be mixed. Such complexity increases the cost and reduces the reliability of these systems. Second is the cost, bulk and weight of the liquid concentrate itself. The cost of the concentrate is substantial due to the cost of the concentrate manufacturing equipment and the labor costs associated with operating this equipment. The cost of concentrate purchased from third party vendors is even higher due to the addition of the vendor's profit. The shipping costs are substantial due to the concentrate's volume and weight. Handling costs at the user site are also substantial because the concentrate generally cannot be handled by the regular nursing staff but instead requires use of lift trucks or other such devices.

Accordingly, there remains a need for an improved method and apparatus for preparing dialysate used in hemodialysis therapy.

To fulfill this need, the present invention provides a method and apparatus for creating dialysate solution *directly* from dry chemicals in a *continuous* process at the *user site*, thereby eliminating the intermediate concentrate step and its attendant drawbacks.

The preferred embodiment of the invention includes a drum for containing the dry chemical mix, a conveyor belt, a mixing vessel and monitoring equipment. The drum includes internal baffles that cause the dry chemical to be deposited onto the end of the conveyor belt as the drum rotates. The conveyor belt passes the chemical through a profile-determining gate and into the mixing vessel. The rate at which the belt delivers the dry chemical to the mixing vessel is governed by an electronic circuit that measures the conductivity of the dialysate and adjusts the belt speed as necessary to maintain the dialysate conductivity at a set value.

The preferred mixing vessel is conical in shape, having a wider upper portion and a narrower lower portion. Warm water is introduced in the lower portion of the vessel and flows upwardly to the water surface. As particles of the chemical drop from the conveyor onto the surface, some particles dissolve instantaneously. Other particles, especially larger particles, sink below the surface and gravitate downwardly through the flowing liquid. As a particle sinks to the lower portion of the vessel, it encounters progressively less saline water at a progressively greater flow rate and turbulence. This environment promotes rapid dsssolution of even caked lumps of the chemical. The dissolution process can be speeded further by use of a small stirring device disposed in the mixing vessel.

The dissolved solution (dialysate) flows out the mixing vessel and into a flow controller which regulates the rate at which dialysate is supplied to the downstream dialysate equipment. A restriction in the flow controller serves as a nucleation site for bubble formation. A downstream deaeration pump causes the dialysate to be degassed.

If it is necessary to adjust the pH of the dialysate solution, a small pump, such as a peristaltic pump, a roller pump, or a cylinder type pump, can be used to inject an acidic fluid at a controlled rate into the warm water provided to the mixing vessel. Such a pump can be driven from the same shaft that is used to drive the conveyor belt carrying the dry chemical mix.

Desirably, two spaced apart pairs of electrodes are used to monitor the dialysate concentration and to regulate the conveyor speed (or other control mechanism) appropriately. The first pair of electrodes measures the conductivity in the mixing vessel itself and thus responds to short term variations in the composition of the dialysate solution. The second pair of conductivity probes measures the conductivity of the dialysate downstream from the mixing vessel and is thus useful in maintaining long term regulation of the dialysate solution composition.

These and other features and advantages of the present invention will be more readily apparent with reference to the detailed description, which proceeds with reference to the accompanying drawings.

BRIEF DESCRIPTION OF THE DRAWINGS

FIG. 1 is a schematic block diagram of a dry chemical mix apparatus according to one embodiment of the present invention.

FIG. 2 is a perspective view of a portion of the apparatus of FIG. 1 showing a mixing vessel, an agitator assembly and part of a conveyor.

FIG. 3 is a sectional view taken along lines 3—3 of FIG. 2 showing the mixing vessel, a flow controller and the agitator assembly.

DETAILED DESCRIPTION OF THE PREFERRED EMBODIMENT

Figure 4:
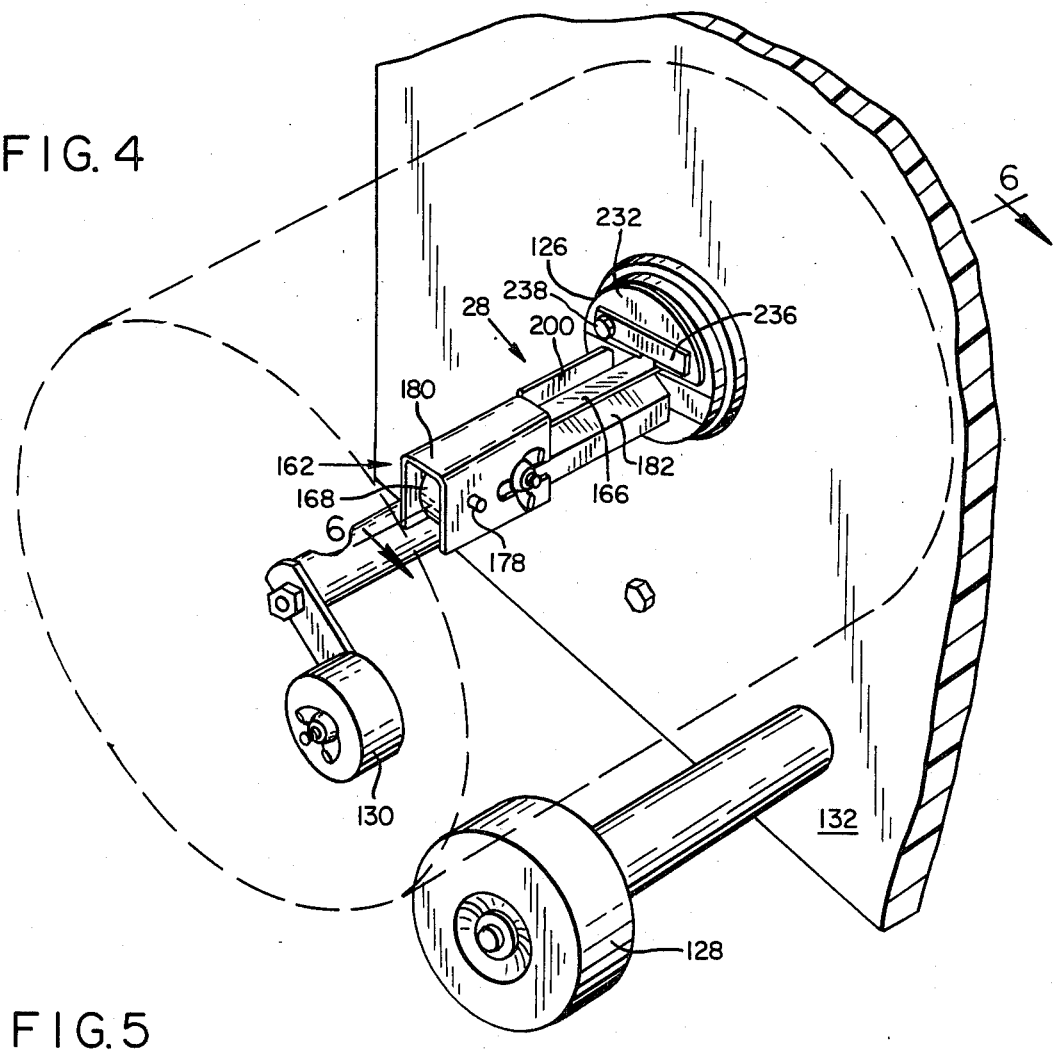
FIG. 4 is a perspective view of another portion of the apparatus of FIG. 1 showing the other end of the conveyor and a drum driving system.

With reference to FIG. 1, a dry chemical mix system 20 according to the present invention includes a source 22 of dry chemical dialysate mix, a source 24 of fluid and a mixing vessel 26 for mixing the dry chemical and fluid together. The dry chemical typically comprises a commercially prepared mixture of dialysis salts composed principally of sodium chloride and calcium chloride, together with an assortment of other compounds, such as potassium chloride, magnesium chloride, acetate and dextrose. The fluid typically comprises water at 38 degrees Celsius. A transport system 28 is provided for transporting dry chemical from dry chemical source 22 to mixing vessel 26 at a controlled rate. A pump 30 is provided for introducing fluid from fluid source 24 into mixing vessel 26 through an inlet conduit 31. A pump 32 can optionally be employed to add an acidic fluid from an acidic fluid source 34 into vessel 26 through conduit 31 at a controlled rate when preparing bicarbonate dialysate.

Mixing vessel 26 includes a withdrawal port 36 for withdrawing mixture from the mixing vessel to a flow controller unit 38. Mix system 20 further includes at least one detector 40 for detecting a characteristic of the solution and for producing an electrical output signal corresponding thereto. A second detector 42 can optionally be employed to detect the same characteristic of the solution at a point remote from detector 40. A control system 44 receives the output signal(s) from the detector(s) and varies the rate at which the dry chemical or the fluid is introduced to mixing vessel 26 so as to substantially maintain the detected characteristic of the solution at a desired value.

MIXING VESSEL

Referring now to FIGS. 2 and 3, mixing vessel 26 desirably comprises a tapered vessel having a wider upper portion 52 for receiving dry chemical and a narrower lower portion 54 for receiving the flow of incoming fluid. As particles of the dry chemical introduced from transport system 28 gravitate from the wider upper portion of the vessel down to the narrower lower portion, they encounter progressively greater fluid flow rates and progressively lesser fluid salinity. (At some point, theoretically, the force of gravity carrying each particle downward is precisely counteracted by the force of the water flow pushing the particle upward. Steady state equilibrium, however, is never reached since the particle is continuously dissolving, reducing both its mass and surface area.) Since undissolved particles are never allowed to settle to the bottom, they continue to circulate in the turbulent fluid until they are completely dissolved. The flow rate and salinity profiles inherent in this tapered vessel configuration help contribute to this rapid and complete dissolution of all chemical introduced into the vessel.

Disposed on the inner wall of vessel 26 are two electrodes 40a, 40b that comprise detector 40. The fluid characteristic normally detected by detector 40 is the solution's concentration, detected by monitoring the conductivity of the fluid. When excited with an electrical signal, the current through, and the voltage across electrodes 40a, 40b varies with fluid conductivity according to Ohm's law. These analog signals are coupled to control system 44 (FIGS. 1, 9), which in turn regulates the addition of fluid and/or chemical to vessel 26 so as to substantially maintain the conductivity of the solution at a desired level.

AGITATOR

With reference to FIG. 3, an agitator assembly 60 can be employed to facilitate mixing of the dry chemical and fluid in the mixing vessel. Agitator assembly 60 comprises an electric motor 62, a rotatable shaft 64 and an agitator element 66 disposed on an end of the shaft 64. Agitator element 66 has a first end portion 68, a second, opposite end portion 70 and a side surface 72 extending therebetween. First end portion 68 is coupled to rotatable shaft 64. Second end portion 70 defines an orifice 74 into which liquid can flow. Side surface 72 defines at least one orifice 76 in fluid communication with first orifice 74. Rotation of agitator element 66 by motor 62 through shaft 64 causes liquid to be forcibly expelled out side orifice 76 by centripetal acceleration, which in turn causes liquid to be drawn into first orifice 74. Mixture of the materials in vessel 26 is thereby facilitated. Agitator assembly 60 is held in place by arms 78 attached to the frame of motor 62 and which are adapted to be received by recesses 80 in the upper portion of vessel 26.

FLOW CONTROLLER

Dialysate solution produced in vessel 26 flows out withdrawal port 36 and into an inlet port 82 of flow controller 38. Withdrawal port 36 and inlet port 82 are forced into proximity by a coupling frame 84 comprised of a U-shaped rod 86, a plate 88 and wing nuts 90. A watertight seal between ports 36 and 82 is established by a compressed O-ring 92 disposed between the ports.

Flow controller 38 comprises a float controlled valve formed in the bottom of a molded vessel 98. A float member 104 floating in the dialysate solution in molded vessel 98 regulates the position of a tapered occluding member 100 in an orifice 102 in the bottom of the vessel. A conduit carries the dialysate from orifice 102 to a dialysis machine (not shown). In addition to being a component of the float controlled valve, occluded orifice 102 also serves as a nucleation site for bubble formation. Bubbles formed at this site can be removed by a downstream bubble trap or deaeration pump. An extension 106 of occluding member 100 extends vertically and serves as a handle by which a user can remove float 104 from vessel 98.

Flow controller 38 dynamically regulates the flow of dialysate solution to the downstream dialysis equipment so as to maintain a constant fluid volume in mixing vessel 26. If, for example, the dialysis equipment tries to draw more fluid from flow controller 38 than mixing vessel 26 is able to supply, the fluid level in the flow controller vessel drops. When the fluid level in the flow controller vessel drops, float 104 also drops. When float 104 drops, occluding member 100 drops further into orifice 102, thereby reducing fluid flow out of the flow controller. This reduced fluid flow out of the flow controller causes the fluid level within the flow controller vessel to rise until equilibrium is again established with the fluid level in mixing vessel 26.

DRUM ASSEMBLY

Figure 5:
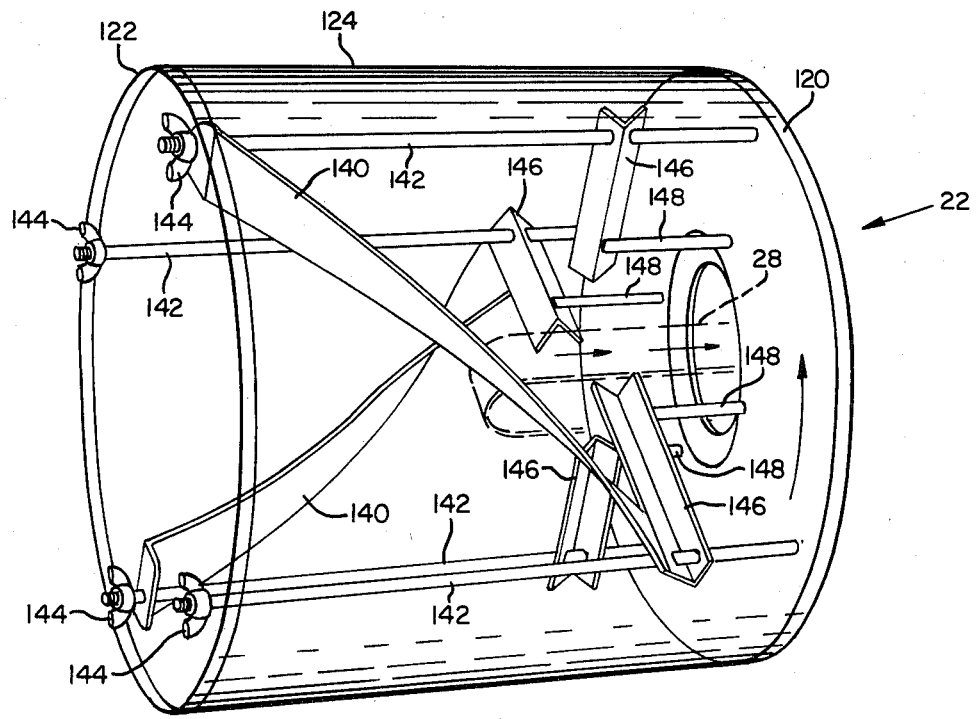
FIG. 5 is a perspective view of a chemical supply drum used in the apparatus of FIG. 1.

Referring now to FIGS. 4 and 5, the dry chemical source used in the preferred embodiment of the present invention comprises a rotatable drum 22. Drum 22 has first and second ends 120, 122 and a cylindrical sidewall 124 extending therebetween. The drum is mounted for horizontal axial rotation on rollers 128, 130 which extend from a panel 132 and on which the drum rests. Roller 128 is driven by a motor (not shown) positioned behind panel 132. Protruding through both panel end 132 and first end 120 of drum 22 is a hub 126 about which the drum rotates. Hub 126 is a component of conveyor 28 and is bolted to conveyor support 133 (FIGS. 2,6), which is in turn attached to panel 132.

Inside drum 22 is at least one vertically inclined blade 140 (FIG. 5) extending along sidewall 124. Each blade 140 lifts dry chemical from the bottom of the drum and causes it to slide towards the first end 120 of the drum as the drum rotates. Each end of each blade is held in place by a rod 142 which extends through the drum and is held in place by a wing nut 144 at second end 122.

Drum 22 further includes at least one radially extending chute member 146 located near first end 120 of the drum. Each chute member 146 lifts dry chemical from the bottom of the drum and directs it onto centrally located conveyor 28 as the drum rotates. Each chute member 146 is fixed in place at its outer end by one of rods 142 and is fixed in place at its inner end by a rod 148.

In addition to their principal functions of transferring dry chemical onto conveyor 28, blades 140 and chutes 146 also serve to agitate and mix the chemical. This can be used to advantage if it is desired to modify a standard, commercially available dry chemical mix with certain additional components. The additional components are simply added to the drum through the opening in first end 120 and the drum rotated for 30 to 60 seconds, within which time complete mixture is effected.

In some applications it may be desirable to effect a change in the dry chemical mix composition *during* the system's operation. As described below, means are provided so that the drum can be removed from the assembly for short periods without interrupting the supply of chemical to mixing vessel 26. Consequently, to change the composition of the dry chemical mix, the drum can simply be removed, the new material added and the drum replaced. Alternatively, an opening can be provided in second end 122 of the drum through which additional material can be added *while* the drum is rotating.

CONVEYOR ASSEMBLY

Referring now to FIGS. 2 and 4–8, the transport system used in the preferred embodiment of the present invention comprises a conveyor assembly 28. Conveyor assembly 28 includes a first end 162 that extends into first end 120 of drum 22 and a second, opposite end 164 which terminates above mixing vessel 26. In operation, conveyor 28 receives dry chemical from chute members 146 as the drum rotates and deposits this chemical into mixing vessel 26.

Figure 6:
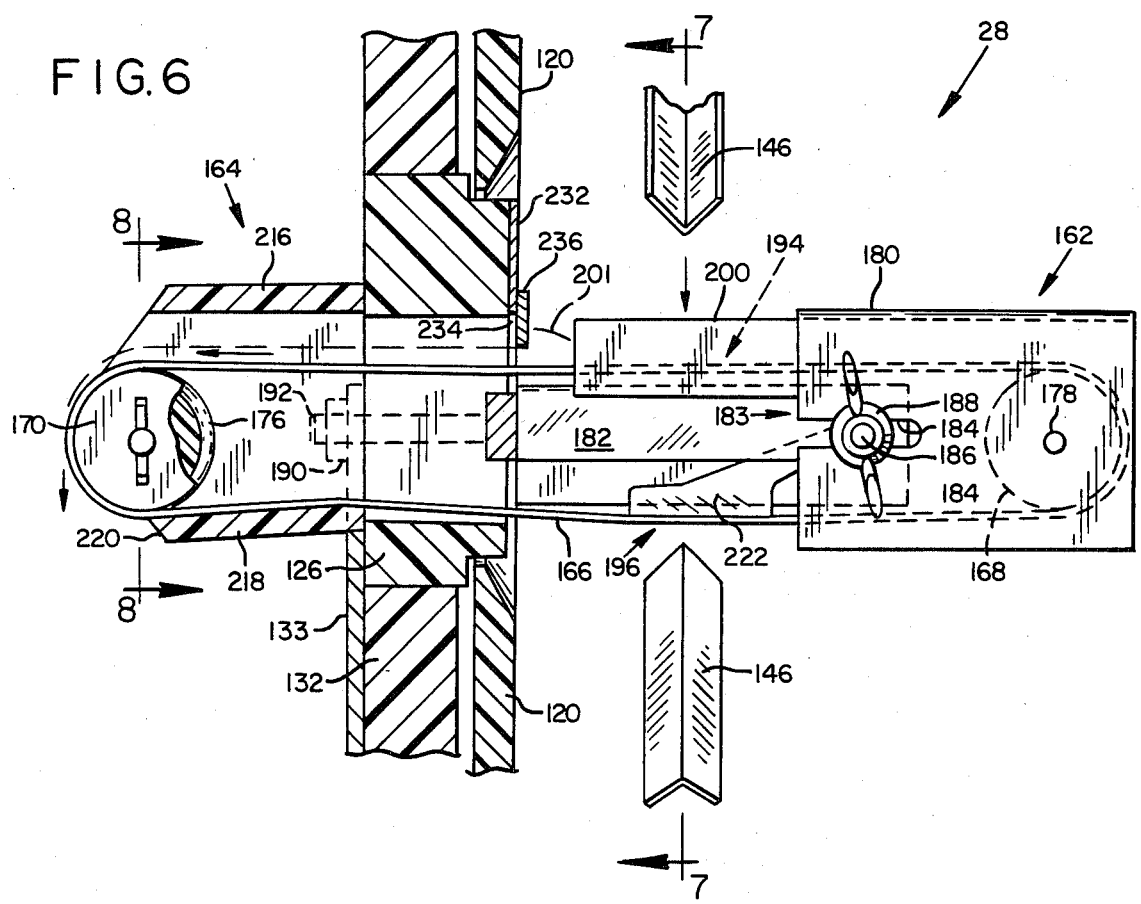
FIG. 6 is a section view taken along lines 6—6 of FIG. 4 showing a material conveyor assembly used in the apparatus of FIG. 1.

Conveyor assembly 28 includes a looped belt 166 and first and second end rollers 168, 170. First end roller 168 is rotatably mounted about a shaft 178 fixedly positioned in an end piece 180. End piece 180 is slidably positioned with respect to a conveyor frame member 182 by a manual slot tensioning mechanism 183. Slot tensioning mechanism 183 comprises a slot 184 in end piece 180, a threaded shaft 186 and wing nuts 188 (FIG. 6). (In alternative embodiments, a spring-loaded self tensioning mechanism could readily be employed). Conveyor frame member 182 links roller 168 to hub 126 and is affixed to the hub by a nut and bolt 190, 192.

Figure 7:
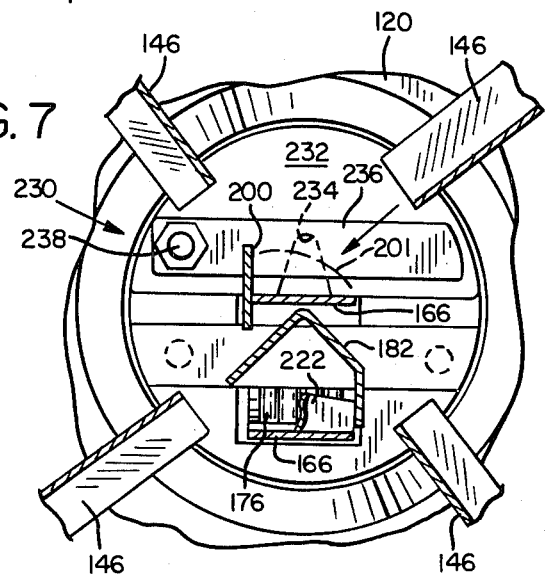
FIG. 7 is a sectional view taken along lines 7—7 of FIG. 6.
Figure 8:
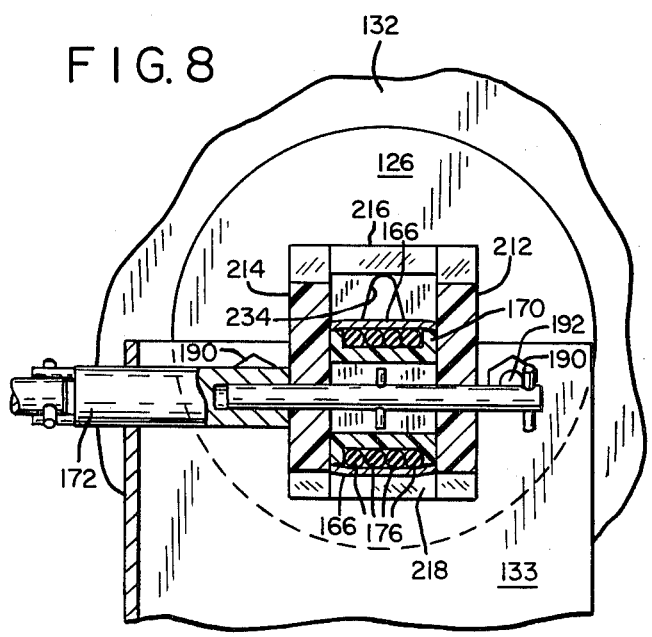
FIG. 8 is a sectional view taken along lines 8—8 of FIG. 6.

Operation of first conveyor roller 168 can be impaired if the hygroscopic chemical mix is allowed to be deposited onto the lower portion 196 of belt 166 as the belt travels in drum 22. Such chemical on the lower portion of the belt can become interposed between the belt and the roller, fouling the roller and interfering with its operation. In order to prevent any chemical from being deposited onto the lower portion 196 of belt 166, conveyor frame member 182 is desirably formed and positioned to serve as a shroud over the lower portion of the belt, as illustrated in FIG. 7. As a further precaution against chemical fouling of roller 168, an angled scraper blade 222 is affixed to frame 182 and impinges against the upper surface of the lower portion of the belt so as to scrape dry chemical residue off the belt.

A back reaction stop member 200 (FIG. 7) is positioned adjacent belt 166 at its first end to accumulate some of the dry chemical that is poured onto belt 166 from chute members 146 as the drum rotates. This arrangement maintains a reserve of dry chemical 201 on the belt so as to prevent the rate of chemical delivery to the mixing vessel from being modulated by the periodic replenishing action of chute members 146. Stop member 200 also allows drum 22 to be removed from the assembly for short periods without interrupting the supply of chemical to mixing vessel 26. During such periods, conveyor 28 simply draws chemical from the reserve of chemical piled on the belt adjacent member 200 with no detectable change in the rate of chemical delivery to vessel 26.

Dry chemical dumped onto belt 166 by chute members 146 passes through a gate, or plow assembly 230 (FIG. 7) which defines the profile of the chemical carried by the belt to the mixing vessel. Gate assembly 230 includes a plate 232 into which is cut an inverted U or V-shaped notch 234. Plate 232 prevents the passage of dry chemical near the edges of the belt, allowing only the material passing through the profile of the centered cutout gate to pass. Mixing vessel 26 is thereby provided with a continuous ribbon of chemical having a constant cross-sectional area. Chemical that does not conform to the profile is pushed off the belt and falls back into the drum.

Gate assembly 230 includes an adjustable member 236 pivotally mounted by a nut and bolt 238 to occlude portions of the cutout gate. By moving the position of adjustable member 236, the profile of dry chemical carried to the mixing vessel can be varied. Although adjustable member 230 is illustrated as being pivotally connected to plate 232 by nut and bolt 238, in alternative embodiments this adjustable member can be moved automatically in response to signals from control system 44 so as to vary the rate at which dry chemical is introduced into the mixing vessel in response to detected changes in the dialysate conductivity.

Since gate assembly 230 regulates the rate at which chemical is supplied to mixing vessel 26, the rotational speed of drum 22, and consequently the rate at which chemical is deposited *onto* the conveyor, is not important. The only constraint on the rotational speed of drum 22 is that it should not be so slow that the chemical reserve accumulated by stop member 200 is exhausted between periodic replenishment by chute members 146 if a steady supply of chemical to the mixing vessel is desired.

On the other end of conveyor 28, second end roller 170 is keyed to a shaft 172 rotated by a motor 174. The speed of motor 174 is governed by control system 44, as discussed below. Frictional engagement between second end roller 170 and belt 166 is enhanced by a plurality of O-rings 176 positioned about a recessed central portion of the second roller. The pressure applied to O-rings 176 by belt 166 causes the O-rings to deform, the outer ones more than the inner ones, thereby forming a slight crown roller which aids in centering of the belt on the roller.

Second end 164 of conveyor 28 is desirably substantially enclosed by side walls 212, 214 and top and bottom walls 216, 218 so as to minimize moisture transfer from the humid atmosphere above mixing vessel 26 back into rotating drum 22. Side walls 212, 214 also aid in centering the belt on second roller 170. Top wall 216 is spaced above belt 166 to permit the desired powder profile to pass unimpeded to mixing vessel 26. Lower wall 218 is adjacent belt 166 and desirably includes an inclined edge portion 220 pressing against the belt as it comes off second roller 170 so as to remove any powder residue that may cling to the belt.

CONTROL SYSTEM

Control system 44 monitors the concentration of the resulting dialysate solution and controls the addition of materials into the mixing vessel to regulate this concentration at a desired level.

Figure 9:
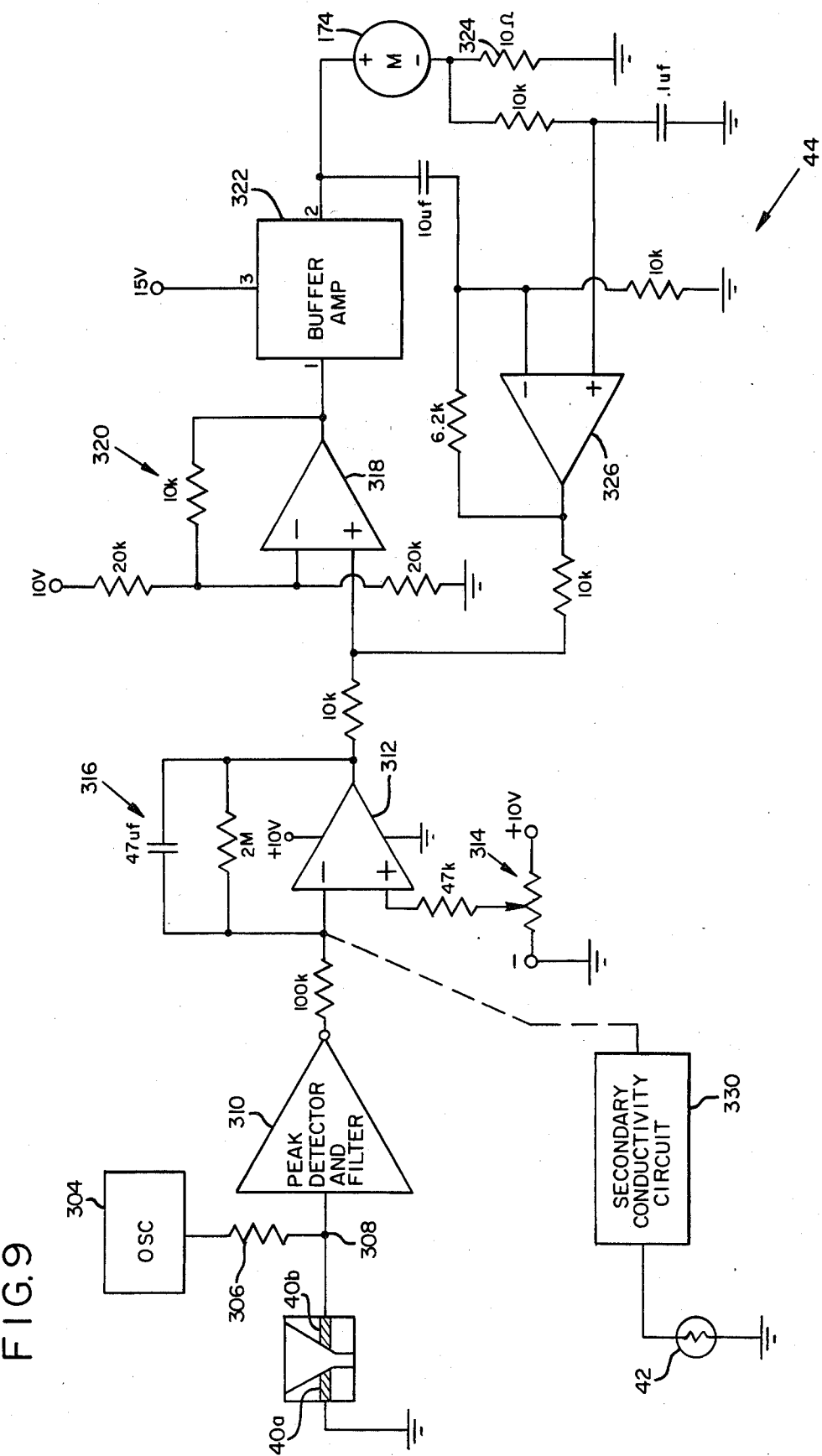
FIG. 9 is a schematic diagram of a control system used in the apparatus of FIG. 1.

In the preferred embodiment, control system 44 controls the speed of motor 174, and consequently the speed of conveyor 28, in response to the detected concentration of the dialysate solution. A schematic block diagram of a suitable control system is shown in FIG. 9.

In the illustrated control system, electrode 40a in mixing vessel 26 is grounded and electrode 40b is excited with an alternating current signal at two kilohertz provided by an oscillator 304 through a voltage dropping resistor 306. The magnitude of the signal provided by oscillator 304 to circuit node 308 is reduced if circuit node 308 is loaded by a low impedance path through the solution in the mixing vessel to ground. Consequently, the signal magnitude at circuit node 308 decreases if the concentration of the solution increases.

The signal at circuit node 308 is fed to an inverting peak detector and filter circuit 310 which rectifies the alternating current signal and produces an output signal inversely proportional to its short term peak value. Peak detector and filter circuit 310 can be a simple resistor-capacitor time delay circuit driving an analog inverter. Alternatively, the peak detection and filtering functions can be omitted entirely, with only a slight degradation in system performance, and a simple analog inverter stage used instead.

The output from inverting peak detector and filter circuit 310 is fed to an LM324 operational amplifier stage 312 configured as a second analog inverter. The noninverting input of amplifier 312 is provided with a bias voltage set by a set point control 314. Set point control 314 is a component of a voltage divider circuit that provides a reference signal establishing the constant value at which the solution concentration is to be maintained. Set point control 314 also allows the concentration of the dialysate to be varied, as desired, during therapy. A conventional feedback circuit 316 is connected from the output of amplifier 312 back to its input to set the gain of the inverting amplifier to the desired value, here twenty.

The output of amplifier 312 is applied to the noninverting input of a second LM324 operational amplifier 318. The inverting input of amplifier 318 is biased by a combination resistive voltage divider and feedback circuit 320.

The output of second operational amplifier 318 is fed to an LM317T buffer amplifier 322 which is a unity gain, high current device used to drive motor 174. The greater the output signal from second amplifier 318, the greater the output signal from buffer amplifier 322 and consequently the faster motor 174 will turn.

The current drawn by motor 174 is sampled by a current sensing resistor 324. The voltage across this resistor is fed back into an LM324 speed stabilization circuit 326. The output of speed stabilization circuit 326 is added to the output of first amplifier 312 at the input of second amplifier 318. This stabilization signal confirms to amplifier 318 that the motor has changed speed in response to changes in dialysate concentration and thereby tends to moderate extreme excursions in the excitation of the motor. (In alternative embodiments, speed stabilization circuit 326 can be omitted entirely with only a slight degradation in performance).

An exemplary operation of the circuit of FIG. 9 may be as follows. The system is initially operating in equilibrium, with the concentration of the dialysate corresponding to the level set by set point control 314. This equilibrium is then disrupted when the operator of the apparatus increases the rate of water flow into the mixing vessel in order to increase the rate at which dialysate is produced.

The increased rate of water flow into the mixing chamber causes the concentration and the conductivity of the resulting dialysate to decrease. The reduced dialysate conductivity reduces the resistive load presented across the output of oscillator 304 and causes the magnitude of the signal at circuit node 308 to rise. Because peak detector and filter 310 is configured as an inverter, the increase in signal magnitude at circuit node 308 causes a decrease in the signal applied to first amplifier 312. Since amplifier 312 is configured to have an inverting gain of twenty, a small signal decrease at its input causes a large signal increase at its output. This increase in output signal is coupled to the noninverting input of amplifier 318, causing the output of this amplifier also to increase. The increased amplitude signal from the output of amplifier 318 is buffered by buffer 322 and fed to motor 174. The increased voltage applied to motor 174 increases its speed. This increase in speed speeds the conveyor system, thereby speeding the rate at which powder is introduced into the mixing vessel. The concentration and conductivity of the resulting dialysate is thereby increased and brought back to its original, desired level.

It should be noted that some of the dry chemical dropped onto the surface of the fluid in vessel 26 by conveyor 28 may be withdrawn immediately through outlet port 36 before it has had an opportunity to dissolve. Consequently, the concentration of the dialysate measured by detector 40 in the dissolution vessel 26 may not accurately reflect the concentration of dialysate ultimately provided to the dialysis machine. Accordingly, it is desirable to measure the concentration of the dialysate using a second detector at a location remote from the mixing vessel, as for example, at some distance past flow controller 38. By the time dialysate reaches this point, any dry chemical flushed out of the mixing vessel with the dialysate will doubtless have dissolved.

As shown in FIG. 9, such a second detector can readily be integrated into control system 44. A second conductivity probe 42, similar in arrangement to probe 40 in mixing vessel 26, is inserted in a remote fluid conduit to measure the conductivity of the solution passing therethrough. This probe is excited by a circuit 330 that includes an oscillator, a voltage dropping resistor and a peak detector/filter identical to that used in connection with the conductivity probes in the mixing vessel. In such a two detector system, the detector in the mixing vessel responds to short-term variations in dialysate composition and the remote detector maintains long-term regulation of the dialysate composition.

As suggested in the discussion of control circuit operation, the rate at which dialysate solution is produced can be varied by manually varying the rate at which water is introduced into the mixing vessel. System control 44 quickly detects any change in dialysate concentration resulting from a change in the rate of water introduction and automatically adjusts the rate of dry chemical introduction accordingly. Thus, it is possible in the illustrated embodiment to vary the rate at which dialysate solution is produced simply by increasing or decreasing the rate at which warm water is introduced into the mixing vessel.

ALTERNATIVE EMBODIMENTS

In an alternative embodiment, control system 44 regulates the dialysate concentration by varying the rate of *water* introduction into vessel 26. In such embodiment, the rate at which dialysate solution is produced can be varied simply by changing the speed at which *conveyor belt* 28 operates. Changes in the rate at which dry chemical is introduced into the mixing vessel causes control system 44 automatically to change the rate of fluid introduction appropriately. Thus, the rate at which dialysate solution is produced can again be easily varied, while the dialysate concentration is maintained substantially constant.

It should be noted that if regulation of the dialysate concentration is effected by regulating the rate of *fluid* introduction into the mixing vessel, control system 44 must be modified somewhat. In the illustrated control system, a detected decrease in dialysate concentration causes the speed of motor 174 to increase so that it provides chemical to the mixing vessel at a faster rate, thereby increasing the dialysate concentration. In contrast, if control over dialysate concentration is effected by controlling the rate of fluid introduction, a detected decrease in dialysate concentration must cause the motor driving the fluid pump to operate at a *slower* rate in order to increase the dialysate concentration. This change in control system response can be implemented by constructing peak detector and filter circuit 310 to be a non-inverting stage, rather than the inverting stage illustrated.

In some embodiments, the pressure at which the fluid is supplied to the apparatus from fluid source 24 may be sufficient to generate an adequate flow of fluid into the mixing vessel without pump 30. In such embodiment, regulation of the fluid flow can be effected by a valve interposed in fluid inlet conduit 31. This valve can be responsive to control system 44 if dialysate concentration is regulated by changing the rate of fluid introduction. If the dialysate concentration is too high, the output signal from the control system can open this valve further, and vice versa.

With certain bicarbonate dialysate solutions, it is desirable to introduce an acidic fluid into the dialysate solution so as to control solution pH and to prevent the sodium bicarbonate from precipitating. As noted earlier, such systems can employ an acidic fluid source 34 (FIG. 1) and a pump 32 for introducing an acidic fluid, such as acetic acid, into fluid inlet conduit 31. Pump 32 is desirably a variable speed pump so that the rate of acidic fluid introduction into the solution can be controlled. In one form of the invention, pump 32 is driven from the same shaft 172 that drives conveyor 28. The ratio of acidic fluid to dry chemical is thus always maintained at a constant value regardless of the speed at which shaft 172 rotates. (In such embodiment, the ratio of acidic fluid to dry powder can be set to a desired value by moving adjustable member 236 on powder gate 230 so as to set the rate of dry chemical delivery for a given belt speed.)

Although the preferred embodiment of the present invention has been described with reference to detectors 40 and 42 that measure the electrical conductivity of the resulting solution, detectors 40 and 42 could alternatively measure other parameters. For example, the detectors could measure the pH or the color of the solution by using conventional techniques. Regardless of what characteristic is detected, control system 44 can be used to responsively alter the rate at which the components being mixed are introduced so as to maintain the detected characteristic at a desired value.

Similarly, although the preferred embodiment of the present invention has been described with reference to a mixing vessel in which the level of fluid is maintained constant by the position of fluid output port 36, alternative arrangements can readily be devised. For example, a fluid output port could be provided in the midportion of the mixing vessel and the level regulated instead by conventional electrical or optical level sensors. If these level detectors detect the fluid level is above a desired level, the rate of fluid withdrawal through the outlet port is increased, and vice versa.

In still other embodiments, fluid output port 36 in the side of vessel 26 can be omitted and the fluid can be allowed instead to overflow the top of the mixing vessel and fall into a surrounding capture vessel. In such a system, the volume of fluid in the mixing vessel is necessarily constant, regardless of changes in flow through the flow controller.

In application, the present invention can be used as a dialysate delivery unit for a single patient dialysis machine or can be used as a central dialysate delivery unit serving several machines. The invention can also be used to retrofit existing dialysis machines, replacing the complex liquid dialysate concentrate proportioning systems currently used with a simpler, more economical dry chemical based system.

Having described and illustrated the principles of our invention in the preferred embodiment, it should be apparent to thse skilled in the art that the invention can be modified in arrangement and detail without departing from such principles. We claim all modifications coming within the scope and spirit of the following claims and equivalents thereof.

We claim:

1. A method for providing dialysate solution to a hemodialysis apparatus comprising the steps:
   introducing a dry chemical dialysate mix to a dissolution vessel at a substantially constant rate;
   introducing a fluid to the dissolution vessel at a substantially constant rate;
   facilitating the dissolution of the dry chemical dialysate mix into the fluid in the dissolution vessel;
   detecting a physical characteristic of the dissolved solution and producing an output signal corresponding thereto;
   providing a reference signal corresponding to a desired value of the physical characteristic;
   comparing the output signal with the reference signal and producing a control signal corresponding thereto;
   adjusting the rate at which the dry chemical dialysate mix or the fluid is introduced to the dissolution vessel in response to said control signal so as to regulate the detected physical characteristic of the dissolved solution substantially to the desired value; and
   continuously removing dissolved solution for supply to the hemodialysis apparatus.

2. The method of claim 1 which further comprises the steps:
   continuously depositing dry chemical dialysate mix onto the surface of a fluid in a wider upper portion of a tapered dissolution vessel; and
   continuously introducing fluid through a fluid introduction port in a narrow lower portion of said tapered dissolution vessel.

3. An apparatus for the on-line preparation of dialysate solution used in hemodialysis therapy directly from a dry dialysate chemical mix comprising:
   supply means for containing the dry dialysate chemical mix;
   a dissolution vessel;
   means for conveying dry dialysate chemical mix from the supply means to the dissolution vessel at a substantially constant rate;
   means for providing dissolution liquid to the dissolution vessel at a substantially constant rate; and
   means for withdrawing dissolved dialysate solution from the dissolution vessel at a substantially constant rate and for making said solution available to a dialysis machine.

4. The apparatus of claim 3 which further comprises means for agitating the dry dialysate chemical mix contained with the supply means to prevent said mix from caking.

5. The apparatus of claim 3 which further comprises means for varying the rate at which either the dry dialysate chemical mix or the dissolution liquid is provided to the dissolution vessel so as to maintain the concentration of the resulting dialysate solution at a substantially constant value.

* * * * *